US008748345B2

(12) United States Patent
Hodge et al.

(10) Patent No.: US 8,748,345 B2
(45) Date of Patent: Jun. 10, 2014

(54) METHOD AND COMPOSITION FOR IMPROVING TURFGRASS

(75) Inventors: Robert L Hodge, Sumter, SC (US); Michael L De Riso, Sugar Land, TX (US)

(73) Assignee: Tessenderlo Kerley Inc., Phoenix, AZ (US)

( * ) Notice: Subject to any disclaimer, the term of this patent is extended or adjusted under 35 U.S.C. 154(b) by 1660 days.

(21) Appl. No.: 12/000,715

(22) Filed: Dec. 17, 2007

(65) Prior Publication Data

US 2008/0280763 A1 Nov. 13, 2008

Related U.S. Application Data

(60) Provisional application No. 60/924,364, filed on May 10, 2007.

(51) Int. Cl.
*A01N 57/12* (2006.01)
*A01N 59/06* (2006.01)
*A01N 59/16* (2006.01)
*A01P 21/00* (2006.01)

(52) U.S. Cl.
USPC .......................... 504/121; 504/194; 504/119

(58) Field of Classification Search
USPC ........................................................ 504/121
See application file for complete search history.

(56) References Cited

U.S. PATENT DOCUMENTS

| | | | |
|---|---|---|---|
| 2,129,013 A | 9/1938 | Linstead et al. | 260/314 |
| 2,214,454 A | 9/1940 | Dent | 260/314 |
| 2,276,860 A | 3/1942 | Niemann et al. | 260/314 |
| 2,452,606 A | 11/1948 | Roselle | 106/289 |
| 2,460,779 A | 2/1949 | Brouillard et al. | 260/314.5 |
| 2,460,783 A | 2/1949 | Lecher et al. | 260/314.5 |
| 2,471,794 A | 5/1949 | Sumner | 260/314.5 |
| 2,485,167 A | 10/1949 | Rintelman | 260/314.5 |
| 2,485,168 A | 10/1949 | Rintelman | 260/314.5 |
| 2,556,729 A | 6/1951 | Bridgeton | 260/314.5 |
| 2,613,128 A | 10/1952 | Baumann et al. | 8/28 |
| 3,379,610 A | 4/1968 | Lyon et al. | 167/22 |
| 3,617,413 A * | 11/1971 | Elbert | 156/61 |
| 3,632,328 A | 1/1972 | Gaskin et al. | 71/3 |
| 3,935,242 A | 1/1976 | Fulconis et al. | 260/429 K |
| 3,950,265 A | 4/1976 | Albrecht et al. | 252/311 |
| 4,049,801 A | 9/1977 | Debourge et al. | 514/129 |
| 4,075,324 A | 2/1978 | Thizy et al. | 424/601 |
| 4,139,616 A | 2/1979 | Ducret et al. | 424/222 |
| 4,394,316 A | 7/1983 | Chao | 260/429 K |
| 4,542,023 A | 9/1985 | Lacroix et al. | 514/126 |
| 4,698,334 A | 10/1987 | Horriere et al. | 514/141 |
| 4,701,209 A | 10/1987 | Sasaki et al. | 504/190 |
| 4,806,445 A | 2/1989 | Horriere et al. | 514/141 |
| 4,923,866 A | 5/1990 | Albert et al. | 514/237.5 |
| 4,956,183 A | 9/1990 | Miki et al. | 424/630 |
| 5,171,853 A | 12/1992 | Thorp et al. | 536/27 |
| 5,206,228 A | 4/1993 | Collins | 514/141 |
| 5,336,661 A | 8/1994 | Lucas | |
| 5,350,843 A | 9/1994 | Itoh et al. | 540/138 |
| 5,380,842 A | 1/1995 | Itoh et al. | 540/128 |
| 5,599,804 A | 2/1997 | Mudge | |
| 5,643,852 A * | 7/1997 | Lucas et al. | 504/126 |
| 5,656,281 A | 8/1997 | Hytte et al. | 424/408 |
| 5,665,672 A | 9/1997 | Lucas | 504/126 |
| 5,747,419 A | 5/1998 | Ishimoto | |
| 6,194,193 B1 * | 2/2001 | Drahos et al. | 435/252.4 |
| 6,287,358 B1 * | 9/2001 | Mason et al. | 71/62 |
| 6,855,668 B2 * | 2/2005 | Milus | 504/309 |
| 6,989,056 B2 * | 1/2006 | Babler | 106/413 |

FOREIGN PATENT DOCUMENTS

| | | |
|---|---|---|
| DE | 24 12 324 | 9/1975 |
| DE | 2511077 | 9/1976 |
| EP | 0 419 915 | 9/1990 |
| FR | 1 562 940 | 3/1969 |
| FR | 2 589 325 | 5/1987 |
| GB | 2 150 027 | 6/1985 |
| JP | 57-034781 | 7/1982 |
| JP | 63-112701 | 5/1988 |
| JP | 1-157904 | 6/1989 |
| JP | 02-138376 | 5/1990 |
| JP | 03-221576 | 9/1991 |
| JP | 6-73397 | 3/1994 |
| JP | 06-321711 | 11/1994 |
| PL | 103345 | 6/1979 |
| WO | WO 89/00079 | 1/1989 |

OTHER PUBLICATIONS

S. Frederiksen et al, Turf Pest Management Handbook, Mallinckrodt Chemical Works, St. Louis, 1966.
S. Lesage, Reduction of the Formation of Ethylenethiourea from Enthylenebis (dithiocarbamates) by Cupric Ions in Aqueous Media, J. Agric. food Chem. 28(4), pp. 787-790 (1980).
A. Stevenson, Fungicidal Compositions, Patent Journal, p. 39 (Jul. 26, 1967).
N. M. Bigelow et al., Phthalocyanine Pigments, The Chemistry of Syntheitc Dyes and Pigments, p. 577-606. (1960).
W.S. Struve, Phthalocyanine Dyes, The Chemistry of Synthetic Dyes and Pigments, pp. 607-624 (1967).
T. Ostmeyer, The Color Green, Golf Course Management pp. 40-44 (Aug. 1994).
M. E. Fenn et al; Studies on the In Vitro and In Vivo Antifungal Activity of Fosetyl-Al and Phosphorous Acid, Phytopathology 74 No. 5, pp. 606-611 (1984).
S. G. Martin et al., Pathogenicity of Rhizoctonia zeae on Tall Fescue and Other Turfgrasses, Plant Disease 67:676 (1983).
S. G. Martin et al., Characterization and Pathogenicity of Rhizoctonia spp. and Binucleate Rhizoctonia-like Fungi from Turfgrass Species, Phtyphathology 74:170 (1984).
L. T. Lucas, Diseases of Warm-Season Grasses, N. C. Agri. Ext. Ser. AG-360 (reprinted) (1987).

(Continued)

*Primary Examiner* — Audrea Buckley
(74) *Attorney, Agent, or Firm* — Hayden Stone PLLC; Christopher G. Hayden

(57) ABSTRACT

A method of improving turfgrass quality involves applying onto the turfgrass an effective amount of a composition which has been dissolved or dispersed in water, wherein the composition contains between 0.11 and 0.14 parts by weight of a phthalocyanine compound, preferably Pigment Green 7, per one part by weight of monoalkyl esters of phosphorous acid or salts thereof, preferably fosetyl aluminum or salts thereof.

16 Claims, No Drawings

(56) References Cited

OTHER PUBLICATIONS

L. B. McCarty et al., Gaeumannomyces Graminis Associated with Spring Dead Spot of Bermudagrass in South Eastern United States, Plant Disease 73:659 (1989).

L. T. Lucas, Diseases of Bentgrass on High-Sand-Content Golf Greens, Plant Pathology Turfgrass Disease Information Note No. 4 (1990).

L. B. McCarty et al., Regrowth of Bermudagrass Infected with Spring Dead Spot Following Low Temperature Exposure, Crop Science 31:182 (1991).

L. T. Lucas, Disease-Like Problems on Turfgrasses in North Carolina, Plant Pathology Turfgrass Disease Information Note No. 5 (1992).

L. T. Lucas, Diseases of Tall Fescue, Plant Pathology Turfgrass Disease Information Note No. 6 (1992).

L. T. Lucas, Long-Term Turf management Practices for Prevention of Turf Diseases, Plant Pathology Turfgrass Information Note No. 7 (1992).

L. B. McCarty et al., Spring Dead Spot Occurrence in Bermudagrass Following Fungicide and Nutrient Applications, Hort. Science 27:1092 (1992).

Gullino et al., Chemical control of dollar spot and brown patch of turfgrass in Italy, Mededelingen—Faculteit Landbouwkundige en Toegepaste Biologische Wetenschappen, Universiteit Gent, 1995, 60, 2b Proceedings, 47th International Symposium on Crop Protection, pt. 2, 1995, 367-70.

Rule 132 Declaration of Leon T. Lucas and Laurence C. Mudge dated Jan. 12, 1994, with Appendices 1-7, filed in U.S. Appl. No. 08/003,632 (U.S. Patent No. 5,336,661).

Supplemental Rule 132 Declaration of Leon T. Lucas and Laurence C. Mudge, dated Mar. 25, 1994, with Appendices 8-9, filed in U.S. Appl. No. 08/003,632 (U.S. Patent No. 5,336,661).

Fore, Specimen Label (Apr. 1985).

CHIPCO Aliette WDG, Specimen Label (1992).

Ingredients in Rohm and Haas Co. Foretm Fungicide (Jul. 24, 1991), from http://www2.siri.org/msds/f2/bzz/bzzsc.html.

\* cited by examiner

METHOD AND COMPOSITION FOR IMPROVING TURFGRASS

This application claims priority from Provisional Application 60/924,364 filed on May 10, 2007.

FIELD OF THE INVENTION

The invention relates to a method of improving turfgrass quality comprising applying an effective amount of a composition containing one part by weight of monoalkyl esters of phosphorous acid, or salts thereof, preferably an aluminum salt of a $C_2$ to $C_4$ alkyl phosphite, more preferably fosetyl aluminum, and between 0.11 and 0.14 parts, more preferably between 0.12 and 0.13 parts by weight of a copper phthalocyanine compound, preferably pigment Green 7, to the turfgrass.

BACKGROUND OF THE INVENTION

Phthalocyanines are known pigments having many applications, such as colorants for inks and coatings and even for turfgrass paints. It is generally known to color turf. U.S. Pat. No. 5,747,419 describes the use of iron containing dyes. Many turf colorants were in the marketplace, though most pigments used were proprietary. See, e.g., J. Van Dam and K. Kurtz, "A Turfgrass Colorant Study," published in the Summer 1971 edition of California Turfgrass Culture, where a variety of proprietary blends were tested, including Stayzgreen™, Greenstuff™, Greenzit™, Sta-Green™, Everbright™, and others. Most colorants are green and blue, and a high percentage of them are used for cosmetic greening golf courses. Using a green indicator to spray the course with pesticides accentuates the green grass, making it look robust and healthy. DE 2,511,077, which published in 1976, claimed a method for coloring a lawn using a phthalocyanine dye. Label information states that the Regreen™ turf colorant available from Precision Laboratories contains a copper phthalocyanine pigment.

Copper phthalocyanine has been used in combination with monoalkyl esters of phosphorous acid, or salts thereof, either with or without mancozeb. U.S. Pat. No. 5,643,852 describes a method of enhancing turf quality in turfgrass by applying in specific ratios certain phthalocyanines in combination with (i) phosphorous acid or an alkaline earth metal salt thereof or certain monoester salts of phosphorous acid and (ii) certain ethylene bisdithiocarbamate contact fungicides. U.S. Pat. No. 5,336,661 discloses using on turfgrass formulations comprising 1 part of certain monoester salts of phosphorous acid, for example fosetyl-Al (preferably Aliette™) and 1.5 to 2.5 parts of mancozeb (preferably FORE™). The FORE™ brand of mancozeb contains 70% mancozeb and 1-2% of copper phthalocyanato(2-). See http://www2.siri.org/msds/f2/bzz/bzzsc.html, for ingredients in Rohm and Haas Co.'s FORE™ FUNGICIDE, 62440.

Of particular interest is U.S. Pat. No. 5,599,804 which describes a method of combating fungi and enhancing turf quality in turfgrass by applying in specific ratios, in particular between 0.01 and 0.1 parts of phthalocyanines (in particular pigment Blue 15) in combination with one part of phosphorous acid or an alkaline earth metal salt thereof or with certain monoester salts of phosphorous acid. The examples in U.S. Pat. No. 5,599,804 do not tell how much of the pigment blue was present, but we believe the amount was about 0.03 to 0.04 parts of pigment Blue 15 per part of fosetyl-Al.

The commercial product is believed to contain only about 4% of phthalocyanine compound, and it seems that this phthalocyanine compound is pigment Blue 15. In tests of this product, the color was found to be not natural appearing, and short-lasting. By short-lasting with normal weather the color is visibly depleted in a week and very faded in two to three weeks.

We have found that turfgrass treated with a commercial formulation above and with formulations such as described in U.S. Pat. No. 5,599,804 do not provide turfgrass that is natural looking. Further, the color dissipates in about a week, which is substantially shorter than the interval at which turfgrass is to be treated with the fungicide. However, there are a number of reasons why no manufacturer has made a product having more phthalocyanine dye. First, custom dictates that the fosetyl-Al product be provided at a concentration of about 70% by weight, and it is generally thought that the surfactants and dispersants needed to formulate this fosetyl-Al with even 4% of phthalocyanine dye does not leave much weight available for the formulation. Second, at amounts above 0.1 parts phthalocyanine dye, at the recommended dosage of fosetyl-Al, a formulation containing most phthalocyanine dyes is unacceptably phytotoxic. Indeed, at the recommended dosage of fosetyl-Al, a formulation containing even 0.1 parts of the preferred pigment Blue 15 of U.S. Pat. No. 5,599,804 is unacceptably phytotoxic.

SUMMARY OF THE INVENTION

The present invention provides a method of improving turfgrass quality comprising applying an effective amount of a treatment composition, which is dissolved/dispersed in water, said treatment composition containing one part by weight of monoalkyl esters of phosphorous acid, or salts thereof, preferably fosetyl aluminum, and between 0.11 and 0.14 parts by weight, more preferably between 0.12 and 0.13 parts by weight, and most preferably between 0.121 and 0.126 parts by weight of a phthalocyanine compound. The most preferred composition for use in this method is a solid water-dispersible/dissolvable powder that consists or consists essentially of: a) about 70%, for example between 69.5% and 71%, by weight fosetyl-aluminum, CAS 39148-24-8, also known as Aluminum tris(O-ethylphosphonate)); b) between 8.4 and 9 parts Pigment Green 7 (as the pigment); c) between 13% and 22% total of surfactants and dispersants, typically between 5 and 10% surfactants and between 8 and 12% dispersants; and d) minor amounts of one or more of defoamers, nutrients, micronutrients, acids, binders, and the like. This solid water-dispersible/dissolvable composition is tank-mixed with water to give a formulation sufficiently diluted to apply onto turfgrass. Typical application rates are 4 to 20 pounds of the solid water-dispersible/dissolvable composition per acre of turf.

Preferred monoalkyl esters of phosphorous acid include the acid form and/or agriculturally acceptable salts of [Al—(O-alkylphosphonate)], [Al—(O-alkylphosphonate)$_2$], or [Al—(O-alkylphosphonate)$_3$], where the alkyl group contains between 2 and 4 carbon atoms, where different alkyl groups may be present in the same compound but typically all alkyl groups in a compound are the same.

The present invention also provides a method of treating turfgrass using a solid water-dispersible/dissolvable treatment composition that contains one part by weight of monoalkyl esters of phosphorous acid, or salts thereof, preferably an aluminum salt of a $C_2$ to $C_4$ alkyl phosphite, more preferably fosetyl aluminum or "fosetyl-Al", and at least 0.105 parts, preferably at least 0.11 parts, and most preferably at least 0.12 parts, for example between 0.121 and 0.128 parts, of a phthalocyanine compound that is primarily, and preferably exclusively, pigment Green 7. Most advantageously, the invention provides a method of treating turfgrass, and also a solid water-dispersible/dissolvable treatment composition, containing one part by weight of monoalkyl esters of phosphorous acid, or salts thereof, preferably an aluminum salt of a $C_2$ to $C_4$ alkyl phosphite, more preferably fosetyl aluminum, and between 0.11 and 0.14 parts, more preferably between 0.12 and 0.13 parts, of a phthalocyanine compound that is primarily, and preferably exclusively, pigment Green 7 per part of the monoalkyl esters of phosphorous acid, or salts thereof. In preferred embodiments, the phthalocyanine compound is primarily Pigment Green 7 (also known as Phthalocyanine Green 7) such that the treatment composition contains, per part of monoalkyl esters of phosphorous acid or salts thereof, at least 0.1 parts, preferably at least 0.11 parts, more preferably at least 0.12 parts, and most preferably at least 0.121 parts of Pigment Green 7.

Advantageously the above-described solid water-dispersible/dissolvable composition comprises at least 50%, more preferably at least 60%, for example at least 67% by weight of said monoalkyl esters of phosphorous acid, or salts thereof. Even more advantageously the above-described solid water-dispersible/dissolvable composition comprises nominally 70% by weight of said monoalkyl esters of phosphorous acid, or salts thereof. By "nominally" we mean within 2%, that is, from 68% to 72%, but typically the composition is controlled to 69.5% and 70.5%, usually between 69.9% and 70.1% by weight.

The most preferred commercial embodiment of the solid water-dispersible/dissolvable treatment composition comprises between 69.5% and 70.5% of fosetyl-Al and between 0.122 and 0.126 parts by weight of a phthalocyanine compound (per part of fosetyl-Al) that is primarily, and preferably exclusively, pigment Green 7.

Blue pigments, for example Pigment Blue 15, if present, are preferably present in an amount less than 0.2 parts per part of fosetyl-Al.

The above-described solid water-dispersible/dissolvable composition further comprises at least one surfactant or dispersant to be included therein. In preferred embodiments, the above-described solid water-dispersible/dissolvable composition further comprises at least 3%, for example between 6% and 12% by weight of dispersants; or at least 5%, for example between 5.5% and 10%, by weight of surfactants. In most preferred embodiments, the water-dispersible/dissolvable composition comprises nominally 70% fosetyl aluminum, 8.4 to 9% of Pigment Green 7, and both dispersants and one or more surfactants, where the total amount of surfactant and dispersant is between 8% and 23%, preferably between 12% and 21% by weight.

DESCRIPTION OF PREFERRED EMBODIMENTS

All percentages used herein unless specifically stated are percent by weight, and all component amounts recited as "parts" are parts by weight and are usually on a basis of parts per part of the active ingredient, e.g., fosetyl-Al. When salts of components are mentioned, unless otherwise specifically stated, the composition can contain the acid form of the component, one or more agriculturally acceptable salts of the component, or any mixture thereof.

The solid water-dispersible/dissolvable composition can be shipped and/or stored as a powder or as granules. Granules are more preferred, and this will typically require the composition to contain between 0.5% to 4% by weight of a binder agent, more typically between 1.5% and 2.5% of a binder agent.

Any water present in the solid water-dispersible/dissolvable composition as the composition is shipped and stored is considered to be a contaminant. There may be, for example, between 0.3% and 5% of water absorbed or condensed on the composition. However, water weight is not included when determining whether the solid water-dispersible/dissolvable composition contains nominally 70% by weight of monoalkyl esters of phosphorous acid, or salts thereof.

The monoalkyl esters of phosphorous acid, or salts thereof in the solid water-dispersible/dissolvable composition (and in the method of treating turfgrass) can be any of those described for example in U.S. Pat. No. 5,599,804, 5,336,661, or 5,643,852. Preferably, however, at least 90%, more preferably at least 95%, most preferably at least 97% by weight of the monoalkyl esters of phosphorous acid, or salts thereof, which are present in the solid water-dispersible/dissolvable composition consist essentially of or alternatively consist of, technical fosetyl-Al (with the trace compounds normally associated with technical Fosetyl-Al). Fosetyl-Al is commercially available from a number of sources, and is typically sold as "Technical Grade" which contains about 96% to 99% by weight fosetyl-Al and a variety of normally present contaminants, inerts, and the like.

The phthalocyanine compound in the solid water-dispersible/dissolvable composition (and in the method of treating turfgrass) comprises at least 0.09 parts, preferably at least 0.10 parts, more preferably at least 0.11 parts, and most preferably at least 0.12 parts, for example between 0.121 and 0.128 parts, of pigment Green 7 per part of the monoalkyl esters of phosphorous acid, or salts. The remaining phthalocyanine dye in the composition (and in the method of treating turfgrass) can be of any suitable type, including pigment Blue 15 and/or Pigment Green 36. Preferably, however, the phthalocyanine dye in the solid water-dispersible/dissolvable composition (and in the method of treating turfgrass) consists of, or consists essentially of, pigment Green 7. By consists essentially of we mean that other phthalocyanine dyes such as pigment Blue 15 may be present but not in an amount that visibly changes the hue of the turfpaint, when applied on turf. The hue is visibly changed if seven of ten non-color-blind people can discern a difference side by side comparisons with a in the color when the normal treatment strength (8 ounces per 1000 square feet) is applied on the turf.

The most preferred commercial embodiment of the solid water-dispersible/dissolvable treatment composition comprises between 68% and 70.5% of fosetyl-Al and between 0.122 and 0.126 parts by weight of a phthalocyanine compound (per part of fosetyl-Al) that is primarily, and preferably exclusively, pigment Green 7.

Generally, the type and amount of surfactants and dispersants in a treatment composition are not particularly critical, and formulation of useful surfactant/dispersant mixtures is within the skill of one in the art given the benefit of this disclosure. However, to manufacture a solid water-dispersible/dissolvable composition having at least 68%, preferably at least 69%, and typically at least 69.5% by weight of said monoalkyl esters of phosphorous acid, or salts thereof, and also including at least 0.115 parts of a phthalocyanine compound (per part of said monoalkyl esters of phosphorous acid, or salts thereof), the type and amount of surfactants and dispersants becomes critical. It is difficult to manufacture an agriculturally and commercially acceptable solid water-dispersible/dissolvable composition having at least 67%, preferably at least 68%, and typically at least 69.5% by weight of fosetyl-Al and also including at least 8.4 to 9 parts of a phthalocyanine compound per part of fosetyl-Al (each having their own inerts, contaminants, and additives which are typically present), as there is very little room in the composition for the required surfactants and dispersants.

The surfactants are advantageously non-ionic surfactants. A preferred surfactant comprises an ethoxylate-type additionally comprising an aromatic moiety and an alkyl (fatty acid) moiety, for example a tristyryl phenol ethoxylate, a castor oil ethoxylate, or mixtures thereof. Advantageously there is an average of between 15 and about 50, more preferably between 30 and 40, moles of ethoxy moieties per surfactant molecule in said ethoxylate-type surfactant. A particularly preferred non-ionic surfactant is tristyryl phenol ethoxylate sold under the tradename "Makon TSP 40"™ available from Stepan Company, which can advantageously be present in an amount for example between about 5% and 8%, preferably between about 5.5% and about 6.5% by weight. Alternatively or additionally, the surfactant can comprise a block polymer-type surfactant such as a polyoxypropylene-polyoxyethylene block copolymer. Agriculturally acceptable block copolymer-type non-ionic surfactants are known in the industry. A particularly preferred block copolymer-type non-ionic surfactant is "Pluronic™ P-104 available from BASF.

In the most preferred embodiment, the solid water-dispersible/dissolvable composition comprises both an ethoxylate-type non-ionic surfactant comprising an aromatic moiety and an alkyl (fatty acid) moiety, for example a tristyryl phenol ethoxylate, and a block copolymer-type non-ionic surfactant.

The dispersants are advantageously condensates of alkylnaphthalenesulfonates. An exemplary composition contains Morwet D 425, a sodium alkylnaphthalenesulfonate formaldehyde condensate. Other dispersants, particularly those normally used in agricultural compositions of phthalocyanine dyes, can be used. The proprietary dispersants in Sunfast™ Green 7 (Sun Chemical Inc.) special 60% pigment formulation work well when incorporated into the formulations of this invention.

Binding agents can be any known in the art, and sugars such as sucrose are useful. The composition can contain a minor amount, typically 0.01% to 0.2% by weight, of various micronutrients such as bioavailable iron, magnesium, sulfur, sulfate, and/or zinc. The composition can contain a minor amount, typically 0.01% to 0.2% by weight, of various nutrients such potassium, bioavailable nitrogen-containing compounds, and phosphates.

Formulations containing high amounts of pigment Blue 15 (~1 part or more per part of Fosetyl-AL) proved unacceptably phytotoxic. A formulation containing Blue 29 resulted in a dull, grayish hue to the formula, most likely the result of the pH. Green 7 is a very popular product for turf, but some customers have indicated that the shade of green is somewhat artificial looking. Thalogreen 36, an EPA registered, bromine-containing pigment, provides a "Kelly green" tint with a hint of yellow. However, the cost is several times the cost of Green 7.

The composition may or may not contain other fungicides and pesticides, and in particular may or alternatively does not contain mancozeb.

An exemplary formulation is shown in Table 1.

TABLE 1

| Turf Fosetyl-Aluminum Granule | | |
|---|---|---|
| Exemplary compounds | Ingredient | % By Wt |
| Fosetyl Aluminum (as 100% active) | Active Ingredient | 69.5-71 |
| Tristyryl Phenol Ethoxylate, Polyoxypropylene-polyoxyethylene Block Copolymer | Surfactants | 5-10 |
| Sodium Alkylnaphthalenesulfonate Formaldehyde condensate | Dispersants | 8-12 |
| Sucrose | Binding agent | 1.5-2.5 |
| Phosphoric Acid (75.0%) | pH Buffer | 0-0.05 |
| Poly dimethylsiloxane Emulsion | Defoamer | 0.01-0.1 |
| Phthalocyanine Green 7 | Active Ingredient | 8.4-9 |
| Fe, Mg, S, sulfate | Micronutrients | 0-1 |
| Ammonia, phosphate, potassium | Nutrients | 0-2 |

The resulting product can be a powder, a wet cake, or a ready to use dispersion concentrate. If made into a powder, the formulation can be first prepared as a concentrated slurry in water, having between say 30% and 80% water, optionally can be wet milled to reduce particle size and promote mixing, and then can be spray dried. In an alternative manufacturing method, the Fosetyl aluminum and other ingredients, but not the formulated pigment, can be prepared and dried, and the formulated pigment can be mixed therein in powder form.

The compositions according to the invention can contain other ingredients, for example protective colloids, adhesives or thickeners, thixotropic agents, stabilizers or sequestrants, as well as other active materials known to have pesticidal properties, especially certain fungicides, acaricides, and insecticides. More generally, the compositions of the invention can include all kinds of solid or liquid additives which are known in the art of crop protection and horticultural pest control treatments. Other useful surfactants can be of the emulsifying or wetting type and can be ionic or non-ionic. Possible surfactants are salts of polyacrylic or lignosulfonic acids; salts of phenolsulfonic or naphthalenesulfonic acids; polycondensates of ethylene oxide with fatty alcohols or fatty acids or fatty amines or substituted phenols (particularly alkylphenols or arylphenols); ester-salts of sulfosuccinic acids; taurine derivatives, such as alkyl taurates; phosphoric esters; or esters of alcohols or polyoxyethylated phenols.

In a useful commercial version, substantially all of the monoalkyl esters of phosphorous acid, or salts thereof which are present in the composition is fosetyl-Al, with other monoalkyl esters of phosphorous acid, or salts thereof being present only as normal contaminants of the fosetyl-Al, and substantially all of the phthalocyanine compound present in the composition is pigment Green 7 Thalogreen 36, or mixture thereof. More preferably, the composition comprises between 69.5% and 70. % fosetyl-Al and 8.69% to 8.82% pigment Green 7.

The present invention can be practiced with all turfgrasses, including cool season turfgrasses and warm season turfgrasses. Examples of cool season turfgrasses are bluegrasses such as Kentucky bluegrass, rough bluegrass, Canada bluegrass, annual bluegrass, upland bluegrass, wood bluegrass, and bulbous bluegrass; the bentgrasses such as creeping bentgrass, colonial bentgrass, velvet bentgrass, South German Mixed Bentgrass, and redtop; the fescues such as red fescue, creeping fescue, chewings fescue, sheep fescue, hard fescue, hair fescue, tall fescue, meadow fescue; the ryegrasses such as annual ryegrass, perennial ryegrass, italian ryegrass; and the wheatgrasses such as fairway wheatgrass, crested wheatgrass, and western wheatgrass. Other cool season turfgrasses include beachgrass, smooth bromegrass, orchardgrass, weeping alkaligrass and crested dog's-tail.

Examples of warm season turfgrasses include Bermudagrass, zoysiagrass, St. Augustine grass, centipedegrass, carpetgrass, Bahia grass, Kikuyugrass, buffalo grass, Blue gramma, seashore *paspalum* and sideoats grama.

In general the rate of application of the formulation of this invention is between 0.05 to 16 ounces per 1000 square feet, more preferably between 4 and 12 ounces per 1000 square feet. The compositions of the invention are applied by known methods.

EXAMPLES

An experimental formulation PEX 60019 was prepared. Formula PEX 60019 contained greater than 70.4% active fosetyl aluminum (the product contained more than 72.178% by weight of technical Fosetyl Aluminum which had a purity of 97.6%). The formulation also contained Sunfast™ Green 7, a formulated product containing 60% of phthalocyanine green 7. The composition of this formulation is presented in Table 2 below.

TABLE 2

Formula PEX 60019

| Trade Name | Chemical Name | Purpose in Formulation | Supplier | % By Wt |
|---|---|---|---|---|
| Tech. Fosetyl-Al (97.6%) | Fosetyl Aluminum | A.I. | | 72.178 |
| Makon ™ TSP 40 | Tristyryl Phenol Ethoxylate Sodium | Surfactant | Stepan Company | 6.428 |
| Morwet ™ D 425 | Alkylnaphthalenesulfonate Formaldehyde condensate | Dispersant | Akzo Nobel | 3.857 |
| Pluronic ™ P-104 | Polyoxypropylene-polyoxyethylene Block Copolymer | Surfactant | BASF | 1.286 |
| Sugar | Sucrose | Binding agent | Savannah Foods | 1.881 |
| Phosphoric Acid (75.0%) | Orthophosphoric acid | pH Buffer | Rhone Poulenc | 0.036 |
| Drewplus ™ L-768 (30%) | Poly dimethylsiloxane Emulsion | Defoamer | Ashland Chemical | 0.046 |
| Sunfast ™ Green 7 (60% pigment) | 60% Phthalocyanine Green 7, 40% dispersants | A.I. | Sun Chemical Corp. | 14.288 |

The ingredients were slurried in water, wherein solids comprised about one half of the total weight, and then the slurry was milled and spray-dried. Subsequent analyses of five random samples of the technical fosetyl aluminum revealed that this ingredient contained 97.6% fosetyl aluminum, 0.4% water, 0.9% sulfate as $SO_4$, 0.6% ammonia as $NH_3$, 0.4% phosphite as $PO_3$, and less than 0.05% chlorides. The Sunfast™ Green 7 contained 60% pigment, with the remainder being proprietary dispersants and possibly surfactants. The PEX 60019 composition therefore contained 70.44% active fosetyl aluminum, 7.71% of a blend of surfactants, 9.57% of a blend of dispersants, and 8.57% of Pigment Green 7. This corresponds to 0.1217 parts by weight of Pigment Green 7 per part of fosetyl aluminum.

The above Formula PEX 60019 was sent to an outside testing company for side-by-side comparison with a commercial product, Chipco Signature™ brand fosetyl aluminum that we believe contains pigment Blue 15, as the control. Both the above formulation and the control formulation were applied to a putting green-like surface having Penncross Bentgrass and scattered *Poa Annua*. The location of the test site was in Georgia. The application rates were 4, 8, and 12 ounces per 1000 square feet. The formulations were applied in mid-morning. During a first series of tests, on the day of application the weather was mostly sunny and the temperature ranged from 74° to 95° F. During a second series of tests, the weather was mostly sunny to partly cloudy and the temperature on the day of application ranged from 74° to 89° F.

At the conclusion of the test, the third party testing service reported that:

1. There was no visual phytotoxicity on plots treated with the control and on plots treated with Formula PEX 60019 at all three application rates.
2. The appearance of plots treated with PEX 60019 was a richer, greener, more life-like color than the plots treated with the control.
3. After five days the color on the plots treated with the control was indistinct. The color on the plots treated with PEX 60019 was still readily visible.
4. After ten days the color on the plots treated with PEX 60019 was still visible, with the color intensity increasing with that application rate.

These positive test results were also confirmed by employees of Tessanderlo Kerley, the assignee of this application.

What is claimed:

1. A method of improving turfgrass quality comprising applying an effective amount of a composition which has been dissolved or dispersed in water to the turfgrass, wherein the composition comprises one part by weight of fosetyl-Al, and between 0.11 and 0.14 parts by weight of Pigment Green 7.

2. The method of claim 1 wherein the composition comprises one part by weight of fosetyl-Al, and between 0.12 and 0.13 parts by weight of Pigment Green 7.

3. The method of claim 1 wherein the composition comprises one part by weight of fosetyl-Al, and between 0.121 and 0.126 parts by weight of Pigment Green 7.

4. The method of claim 1 wherein the composition comprises at least 0.1 parts by weight of Pigment Green 7 per part by weight of fosetyl-Al.

5. The method of claim 2 wherein the composition comprises at least 0.11 parts by weight of Pigment Green 7 per part by weight of fosetyl-Al.

6. The method of claim 3 wherein the composition comprises at least 0.12 parts by weight of Pigment Green 7 per part by weight of fosetyl-Al.

7. The method of claim 1 wherein the composition further comprises Thalogreen 36.

8. The method of claim 1, wherein the composition comprises between 68% to 72% by weight of fosetyl aluminum, between 8.4% to 9% by weight of Pigment Green 7, and between 12% and 21% by weight of dispersants and/or surfactants.

9. The method of claim 8, wherein the composition further comprises bioavailable iron, magnesium, sulfur, sulfate, and/or zinc.

10. The method of claim 8, wherein the composition further comprises 0.01% to 0.2% by weight of potassium, bioavailable nitrogen-containing compounds, and phosphates.

11. The method of claim 1 wherein the composition is applied to the turfgrass at a rate of between 4 and 12 ounces per 1000 square feet.

12. A method of treating turfgrass comprising applying to said turfgrass a treatment composition comprising fosetyl-Al and between 0.11 and 0.14 parts by weight of Pigment Green 7 per part by weight of fosetyl-Al, wherein said composition is applied at a rate of between 4 and 12 ounces of the treatment composition per 1000 square feet of turf grass, wherein said treatment is applied in a water dispersion or solution, and wherein said treatment is not phytotoxic.

13. The method of claim 12 wherein the composition comprises between 0.12 and 0.13 parts by weight of Pigment Green 7 per part by weight of fosetyl-Al.

14. A method of improving turfgrass quality comprising applying an effective amount of a composition which has been dissolved or dispersed in water to the turfgrass, wherein the composition comprises one part by weight of fosetyl-Al, and at least 0.105 parts by weight of Pigment Green 7.

15. The method of claim 14 wherein there is at least 0.11 parts by weight of the Pigment Green 7 per part by weight of the fosetyl-Al.

16. The method of claim 14 wherein there is at least 0.12 parts by weight of Pigment Green 7 present per part by weight of the fosetyl-Al.

* * * * *